(12) United States Patent
Jadhav et al.

(10) Patent No.: US 10,023,891 B2
(45) Date of Patent: Jul. 17, 2018

(54) PROCESS OF CHIRAL RESOLUTION OF CYCLIC AND ACYCLIC ACETATES TO ENANTIOMERICALLY PURE (R)-ALCOHOLS

(71) Applicant: Council of Scientific & Industrial Research, New Delhi (IN)

(72) Inventors: Dipesh Dattu Jadhav, Maharashtra (IN); Nilofer Jahan Khairunnasar Siddiqui, Maharashtra (IN); Swati Pramod Kolet, Maharashtra (IN); Hirekodathakallu Thulasiram, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/033,570

(22) PCT Filed: Nov. 3, 2014

(86) PCT No.: PCT/IN2014/000701
§ 371 (c)(1),
(2) Date: Apr. 29, 2016

(87) PCT Pub. No.: WO2015/063796
PCT Pub. Date: May 7, 2015

(65) Prior Publication Data
US 2016/0281122 A1    Sep. 29, 2016

(30) Foreign Application Priority Data

Nov. 1, 2013  (IN) .......................... 3242/DEL/2013

(51) Int. Cl.
| | | |
|---|---|---|
| *C12P 17/18* | (2006.01) | |
| *C12P 7/04* | (2006.01) | |
| *C12P 7/22* | (2006.01) | |
| *C12N 9/10* | (2006.01) | |
| *C12P 41/00* | (2006.01) | |
| *C12P 7/02* | (2006.01) | |
| *C12P 7/26* | (2006.01) | |

(52) U.S. Cl.
CPC .............. *C12P 17/182* (2013.01); *C12P 7/02* (2013.01); *C12P 7/04* (2013.01); *C12P 7/22* (2013.01); *C12P 7/26* (2013.01); *C12P 41/004* (2013.01)

(58) Field of Classification Search
CPC ..... C12P 7/04; C12P 7/40; C12N 9/88; C12Y 401/01
USPC ...................... 435/136, 132, 135, 195, 254.2
See application file for complete search history.

(56) References Cited

PUBLICATIONS

Mandal et al. J. Mol Cat. B. Enz. 2004 , 27 pp. 61-63.*
Oritani et al., Microbial Resolution of (+/−)-Acyclic Alcohols, Arg. Biol. Chem., 37(8), 1923-1928, 1973 (6 pages).
Alphand et al., "Microbiological Transformations 35: Enantioselective One-step Preparative Scale Synthesis of 1,3-dithiane-1-oxide via Whole-cell Bacterial Oxidation", Tetrahedron Letters, vol. 37, No. 34, pp. 6117-6120, 1996 (4 pages).
Ghanem et al., "Application of Lipases in Kinetic Resolution of Racemates", Chirality 17:1-15 (2005 (15 pages).
Daubmann et al., "Oxidoreductases and hydroxynitrilase Lyases: Complementary Enzymatic Technologies for Chiral Alcohols", Eng. Life Sci. 2006, 6, No. 2, 2006 (5 pages).
Cross et al., Enzymatic esterification of lavandulol—a partial kinetic resolution of (S)-lavandulol and preparation of optically enriched (R)-lavandulyl acetate, Biotechnology Letters 26: 457-460, 2004 (4 pages).
Zada et al., "Enzymatic transesterification of racemic lavandulol: preparation of the two enantiomeric alcohols and of the two enantiomers of lavandulyl senecioate", Tetrahedron: Asymmetry 15 (2004) 2339-2343 (5 pages).
Zada et al., "A convenient resolution of racemic lavandulol through lipase-catalyzed acylation with succinic anhydride: simple preparation of enantiomerically pure (R)-lavandulol", Tetrahedron: Asymmetry 17 (2006) 230-233 (4 pages).
Olsen et al., "Biocatalytic esterification of lavandulol in supercritical carbon dioxide using acetic acid as the acyl donor", Enzyme and Microbial Technology 39 (2006) 621-625 (5 pages).

* cited by examiner

*Primary Examiner* — Tekchand Saidha
*Assistant Examiner* — Mohammad Y Meah
(74) *Attorney, Agent, or Firm* — Blank Rome LLP

(57) ABSTRACT

The patent discloses herein a process for the chiral resolution of racemic cyclic and acyclic acetates to obtain (R)-alcohol. Further, it discloses the resolution of racemic cyclic and acyclic acetates to obtain enantiomerically pure (R)-(−)-alcohol as single enantiomer through fungal catalyzed deacylation in single fermentation, wherein fungal strains are *F. proliferatum*.

6 Claims, 13 Drawing Sheets

PROCESS OF CHIRAL RESOLUTION OF CYCLIC AND ACYCLIC ACETATES TO ENANTIOMERICALLY PURE (R)-ALCOHOLS

FIELD OF THE INVENTION

The present invention relates to a process of chiral resolution of cyclic and acyclic acetates to obtain (R)-Alcohols using whole cell microorganisms.

The present invention further relates to resolution of racemic cyclic and acyclic acetates to obtain enantiomerically pure (R)-Alcohols as single enantiomer through *F. proliferatum* fungal catalyzed deacylation in single fermentation.

BACKGROUND AND PRIOR ART (±)-2-Hexanol and (±)-2-Heptanol are important fragrance compounds as the S enantiomer of 2-Hexanol possess Mushroom, green, ripe, berry, astringent, metallic odour while R enantiomer of 2-Hexanol possess Mushroom, dusty, oily odour. R-2-Heptanol has Fruity, sweet, oily, fatty odour while S-2-Heptanol has Mushroom, oily, fatty, blue cheese, mouldy odour.

R-(−)-2-Hexanol and S-(+)-2-Hexanol were used in preparation of some of the key intermediates in the total synthesis of antivirally active glycolipid cycloviracin $B_1$.

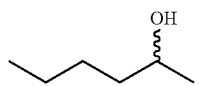

While R-(−)-2-heptanol is used in resolving the diastereoisomeric mixture of a key intermediate in the synthesis of 1-(2-chloro-4-pyrrolidin-1-ylbenzoyl)-2,3,4,5-tetrahydro-1H-1-benzdiazepine, known to be a strong vasopressin $V_2$ receptor agonist.

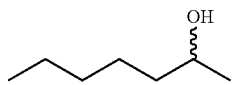

(±)-Lavandulol is an important terpene constituent in plants and has also been found in insects. It is chemically known as 2-isopropylpentyl-5-methyl-4-hexen-1-ol, and is represented by the structural formula as shown below.

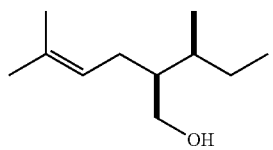

(±)-Lavandulol and its simple esters, are minor, but important constituents of essential oils. These are common ingredients in the cosmetic industry. The (R)-form is a constituent of French lavender oil, which is used in the perfume chemistry. The fragrance of the nature identical (R)-enantiomer ('weak floral, herbal odor with slightly lemon-like, fresh citrus fruity nuance') was superior to those of both the unnatural (S)-enantiomer ('very weak odor') and the racemate ('weak floral, herbal odor').

Recently, (R)-lavandulol and the different esters of this enantiomer have been identified as sex or aggregation pheromone components in several insects. (R)-Lavandulyl (S)-methylbutanoate is a component of the female sex pheromone of the hibiscus mealybug, (R)-lavandulyl acetate is a component of the male produced sex pheromone of the western flower thrips and (R)-lavandulol is a component of the aggregation pheromone of the strawberry blossom weevil.

Commercially available lavandulol and its acetates are in racemic mixture form. Easy access to the two lavandulol enantiomers is of importance in perfumery because they may display different pharmacological activities and certainly different fragrances and odor thresholds. Therefore, much effort has been made in the synthesis of racemic and chiral lavandulol.

(±)-1-Phenyl ethanol is an important molecule which is used as chiral building block and synthetic intermediates in chemical and pharmaceutical industries. (R)-(+)-1Phenyl ethanol is used as fragrance in cosmetic industry due to mild floral odour and also is used in the preparation of Solvatochromic dye, ophthalmic preservative and inhibitor of cholesterol intestinal adsorption.

(±)-1-Phenyl propanol is also used as flavor and chloeretic agent in cosmetic and pharmaceutical industry.

Oritani, T. et al. (Agr. Biol. Chem. 1973, 37, 1923-1928) describe that microbial asymmetrical hydrolysis of the acetates of the racemic prim-alcohols having an asymmetrical carbon atom at the ß-position gave lower optically active alcohols and the acetates of their antipodes using microorganisms (*Bacillus subtilis* var. Niger, *Trichoderma S*).

An article by Kenji Mori describes the preparative scale enantioselective oxidation of 1,3-dithiane to the corresponding monosulfoxide using whole-cell cultures of two bacteria, i.e. *Acinetobactercalcoaceticus* NCIMB 9871 and *Pseudomonas* sp. NCIMB 9872 (Tetrahedron Letters; Volume 37, Issue 34, 19 Aug. 1996, Pages 6117-6120; doi: 10.1016/0040-4039(96)01306-8; Microbiological transformations 35).

There are some of the recent developments in the rapidly growing field of lipase-catalyzed kinetic resolution of racemates for the separation of enantiomers in presence of biocatalyst (enzyme or a microorganism) or a chemocatalyst (chiral acid or base or even a chiral metal complex). Asymmetric hydrolysis of the racemic binaphthyldibutyrate (the ester) using whole cells from bacteria species afforded the (R)-diol with 96% ee and the unreacted substrate (S)-ester with 94% ee at 50% conversion (Ashraf Ghanem and Hassan Y. Aboul-Enein; Chirality 17:1-15, 2005). According to Thomas Daußmannetal.biocatalytic processes are useful methods for the production of chiral intermediates (chiral alcohol). Biological systems such as whole cell biotransformations with yeast are applied. Recently, enzymatic processes using whole cell fermentation or isolated alcohol dehydrogenases (ADHs) have gained increased interest for the commercial production of chiral alcohols (Engineering in Life Sciences; Volume 6 Issue 2, Pages 125-129; DOI: 10.1002/elsc. 200620910).

Mori et al. used the diastereoselective alkylation of the chiral 3-hydroxy ester as key step for the synthesis of (S)-Lavandulol and (S)-Citronellol. Alternatively, biocatalytic reduction of (3-keto esters) in whole cell processes with bakers' yeast was used.

Hannah Cros et al. describe asymmetric esterification of the racemic primary alcohol lavandulol using lipase B from Candida antarctica and acetic acid as acyl donor in 80% yield. The enantioselectivity of the process was characterized, and a preparative resolution of 25 mm racemic lavandulol, stopped at approx. 55% conversion, yielded (S)-lavandulol and (R)-lavandulyl acetate (Hannah Cros et al; Biotechnology Letters; Springer Netherlands; Volume 26, Number 5/March, 2004; DOI:10.1023/B:BILE.0000018268. 42802.d0; pp 457-460)

AnatZada et al. report the preparation of the two enantiomers of lavandulol and lavandulylsenecioate, starting from racemic lavandulol based on a two-cycle enzymatic transesterification of racemic lavandulol with vinyl acetate using Porcine pancreas lipase. High enantioselectivity was achieved while the preparation yielded (R)-lavandulol with 96.7% ee and (S)-lavandulol with 92.6% ee (Tetrahedron: Asymmetry; Volume 15, Issue 15, 9 Aug. 2004, Pages 2339-2343; doi:10.1016/j.tetasy.2004.06.015). The drawback of the method is the need of lengthy column chromatography in order to separate the unreacted alcohol from the formed acetate.

Further, AnatZada et al. describe a convenient resolution of racemic lavandulol through lipase-catalyzed acylation with succinic anhydride. Porcine pancreas lipase from Sigma or Hog pancreas lipase from Fluka were chosen on the basis of previous screening of different lipases for the resolution of (±)-lavandulol. This method is used for the preparation of enantiomerically pure (R)-lavandulol with 98% ee in one resolution cycle. The (S)-lavandulol with 90% ee can be obtained by a second resolution cycle (Tetrahedron: Asymmetry; Volume 17, Issue 2, 23 Jan. 2006, Pages 230-233; doi:10.1016/j.tetasy.2005.12.021). This process has limitation for the large scale production.

According to Teresa Olsen et al. monoterpenelavandulol has been successfully converted to lavandulyl acetate by enzymatic catalysis in supercritical carbon dioxide using immobilized Candida antarctica lipase B (Novozym 435). Conversions of up to 86% were observed at substrate concentrations of 60 mM at 60° C. and 10 MPa. Increased temperature of the system resulted in lower enantioselectivity, whereas changes in pressure/density had little effect on this parameter (Enzyme and Microbial Technology; Volume 39, Issue 4, 2 Aug. 2006, Pages 621-625; doi:10.1016/j.enzmictec.2005.11.025).

EP 0258666 (A2) relates to the stereoselective transformation of alcohol substrate (lavandulol and analogous alcohols) to the corresponding acid (lavandulic acid) by oxidizing enzymes originating from microorganisms (disclosed three species of *Aspergillus* genus i.e. *Aspergillusochraceus* (ATCC 18500); *Aspergillusflavipes* (ATCC 1030); and *Aspergillusflavipes* (ATCC 11013). These microorganisms contain one or more enzymes which transform the alcohols to the corresponding acid, perhaps as a detoxification mechanism.

In "A convenient resolution of racemic lavandulol through lipase-catalyzed acylation with succinic anhydride: simple preparation of enantiomerically pure (R)-lavandulol" by Anat Zada and Ezra Dunkelblum; Tetrahedron: Asymmetry; Volume 17, Issue 2, 23 Jan. 2006, Pages 230-233, where a commercial Porcine pancreatic lipase is used for converting (±)-Lavandulol to its S-Lavandulol acetate with succinic acid as an Acyl donor in organic solvent.

In our case we have used (±)-Lavandulol acetate as a precursor which when incubated with fungus *F. Proliferatum* gives R-Lavandulol as final product with >95% e.e. Based on the results obtained from GC chromatograms we are predicting involvement of two enzyme systems involved in catalyzing the same reaction. Where first (±)-Lavandulyl acetate is deacylated to form (±)-Lavandulol and then another probable enzyme alcohol Dehydrogenase catalyses conversion of (±)-Lavandulol to R-(−)-Lavandulol. Since our fungal system catalyses conversion of (±)-Lavandulyl acetate to R-Lavandulol in aqueous system rather than in organic solvent as mentioned in prior art. It has advantage of scaling it in large scale fermenter level as whole cells are used over the conventional use of pure enzymes. Use of pure enzymes increase the cost of production over whole cell method as no costly cofactors are needed in this process and enzyme recovery is very low. So the process mentioned by us shows an advantage over that mentioned in prior art.

There is an urgent need of a process for preparing enantiomerically pure (R)-alcohols which is cost effective, simple, and will be useful for the production of (R)-alcohol commercially in large scale.

OBJECTIVE OF THE INVENTION

The main object of the present invention is to provide an easier and cheaper process of producing enantiomerically pure R-Alcohols from racemic cyclic and acyclic acetates by whole cell method.

SUMMARY OF THE INVENTION

Accordingly, the present invention provides a process for the chiral resolution of racemic cyclic and acyclic acetate to obtain enantiomerically pure (R)-Alcohol as single enantiomer comprising the steps of;
i) incubating fungus for 24-48 hrs at temperature ranging between 28° C. to 30° C. in a media;
ii) adding substrates selected from cyclic and acyclic acetates in media of step (i) and incubating further for 6 hrs to 3 days at temperature ranging between 28° C. to 30° C. to obtain enantiomerically pure (R)-Alcohol In an embodiment of the present invention the fungal strains is *F. proliferatum*.

In an embodiment of the present invention spores and mycelia of fungal strains *F. proliferatum* were used.

In one embodiment of the present invention the acyclic acetate is selected from the group consisting of 2-Heptyl acetate, lavandulyl acetate and 2-Hexyl acetate.

In another embodiment of the present invention the cyclic acetate is selected from the group consisting of 1-Phenylethyl acetate, 1-Phenylpropyl acetate.

In another embodiment of the present invention yield of the enantiomerically pure (R)-Alcohol as single enantiomer is in the range of 95-99.9%.

Still in another embodiment of the present invention enantiomerically pure (R)-Alcohol is selected from the group consisting of R-lavandulol, R-2-Hexnol, R-2-Heptanol, R-1-Phenyl ethanol and R-1-Phenyl propanol.

DETAILED DESCRIPTION OF THE INVENTION

Figure 1:
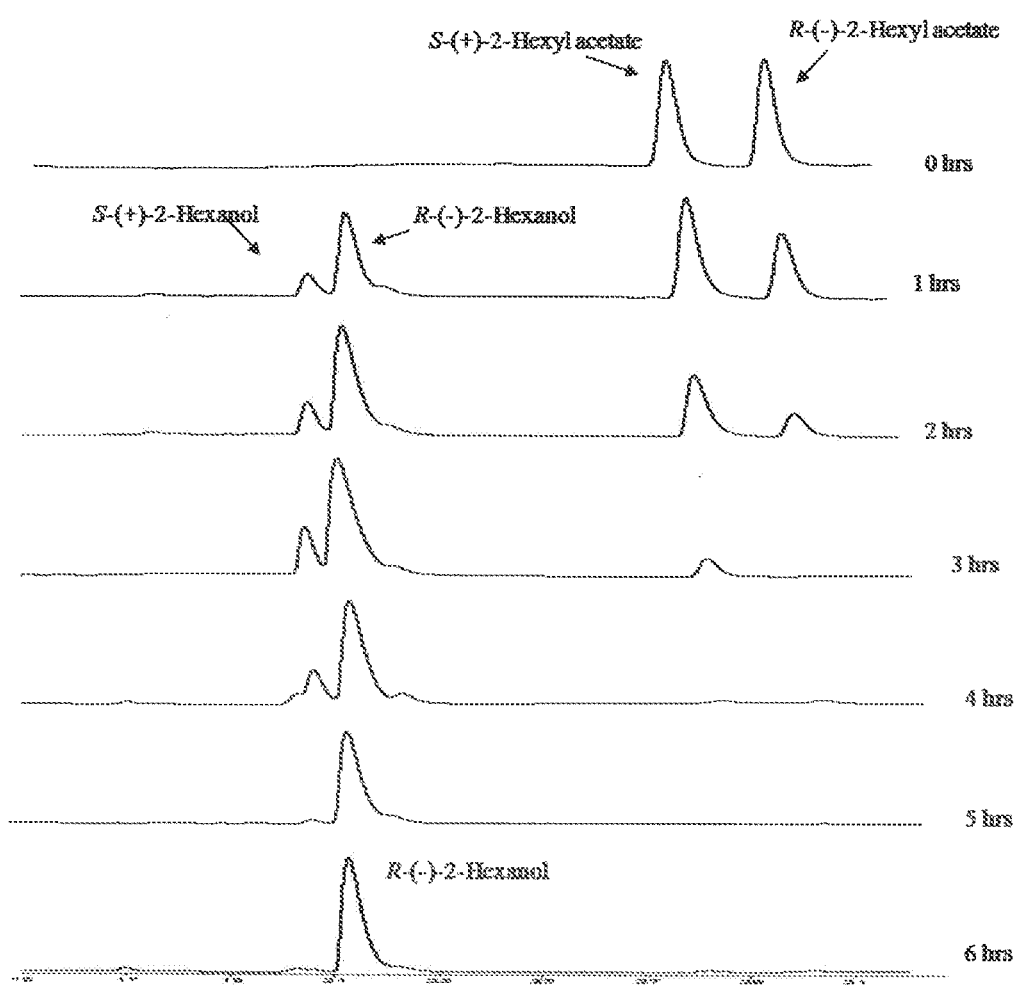
FIG. 1 is a GC chromatogram showing conversion of (±)-2-Hexyl acetate to R-(−)-2-Hexanol by Resting cell experiment over a period of 6 hrs. by *F. proliferatum*.
Figure 2:
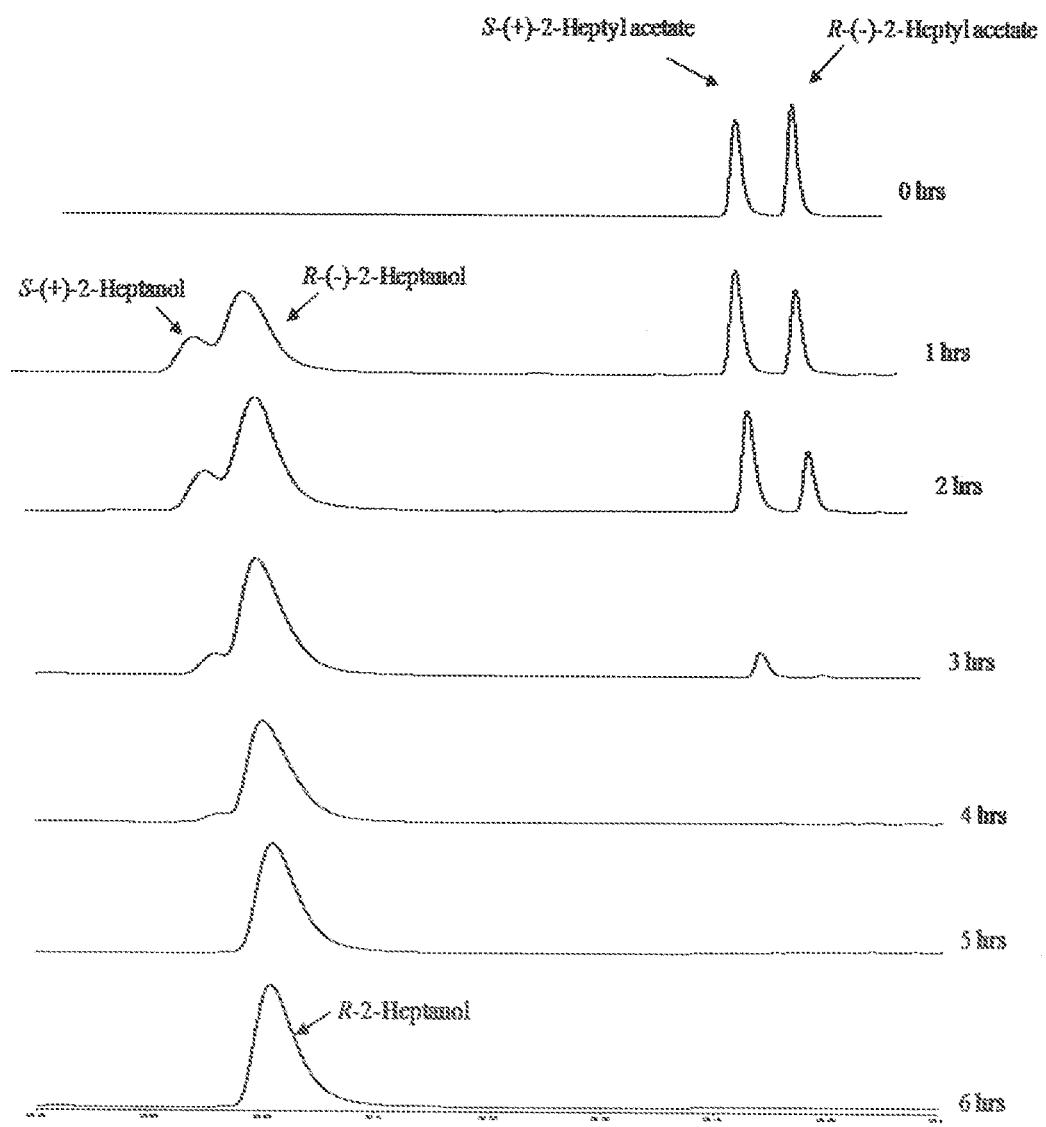
FIG. 2 is a GC chromatogram showing conversion of (±)-2-Heptyl acetate to R-(−)-2-Heptanol by Resting cell experiment over a period of 6 hrs. by *F. proliferatum*.
Figure 3:
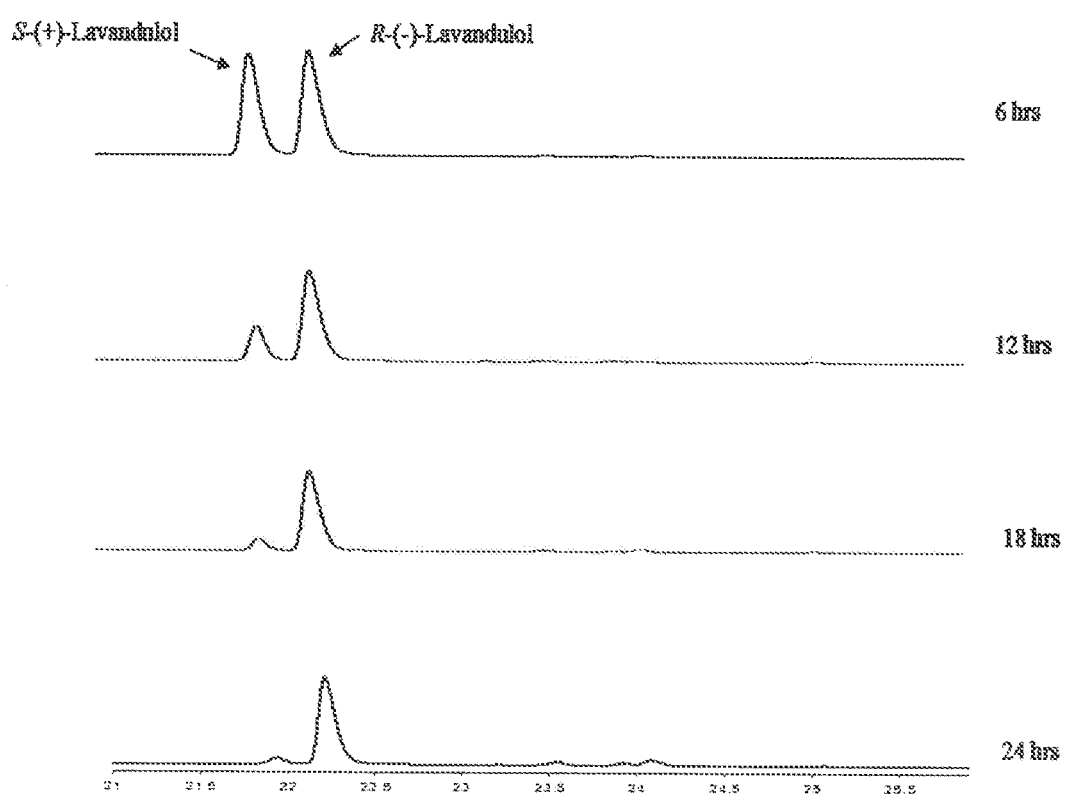
FIG. 3 is a GC chromatogram showing Resting cell experiment with (±)-Lavandulyl acetate.
Figure 4:
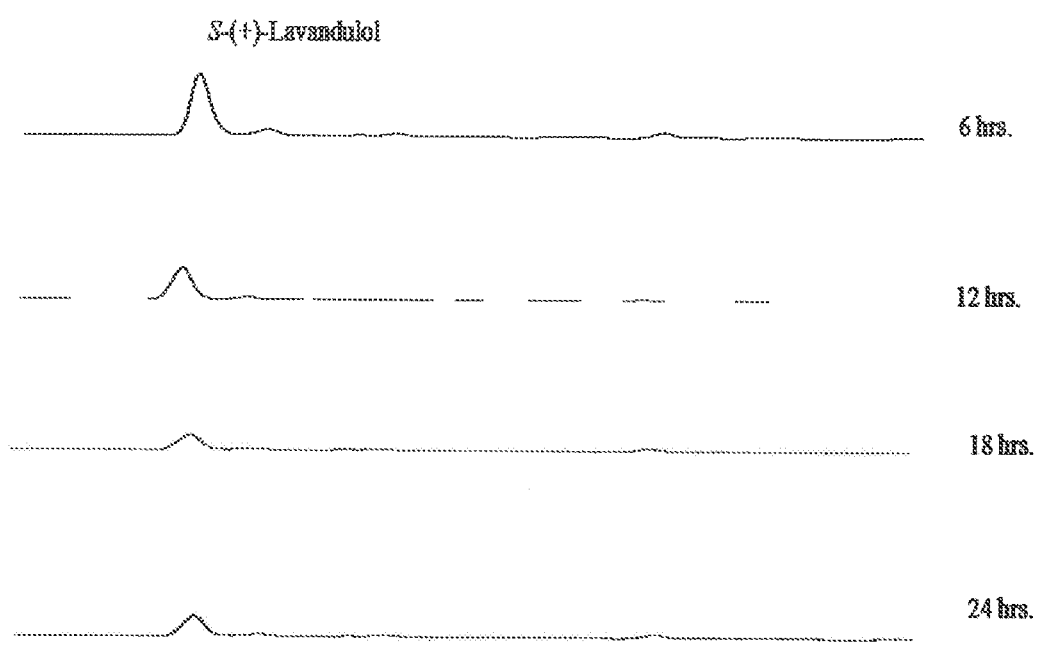
FIG. 4 is a GC chromatogram showing Resting cell experiment with S-(−)-Lavandulyl acetate.
Figure 5:
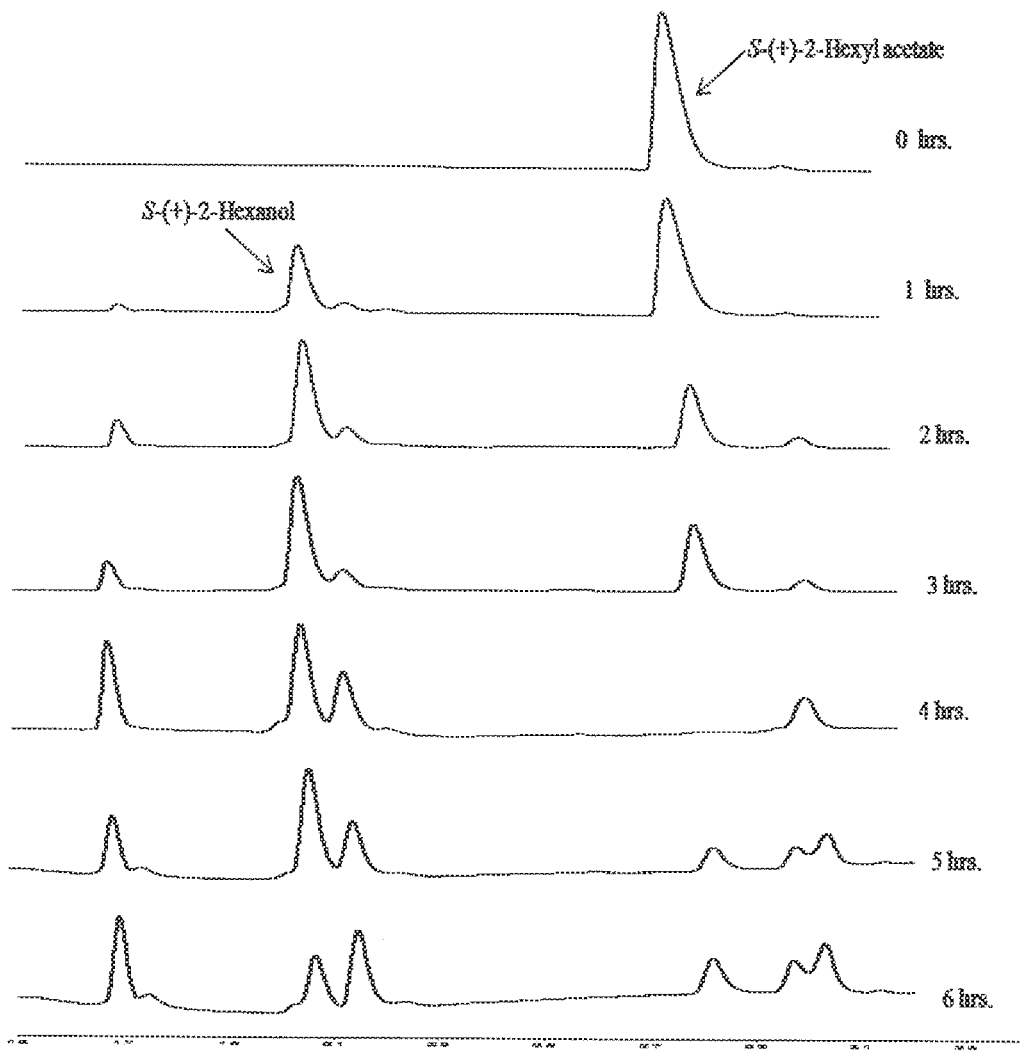
FIG. 5 is a GC chromatogram showing Resting cell experiment with S-(+)-2-Hexyl acetate.
Figure 6:
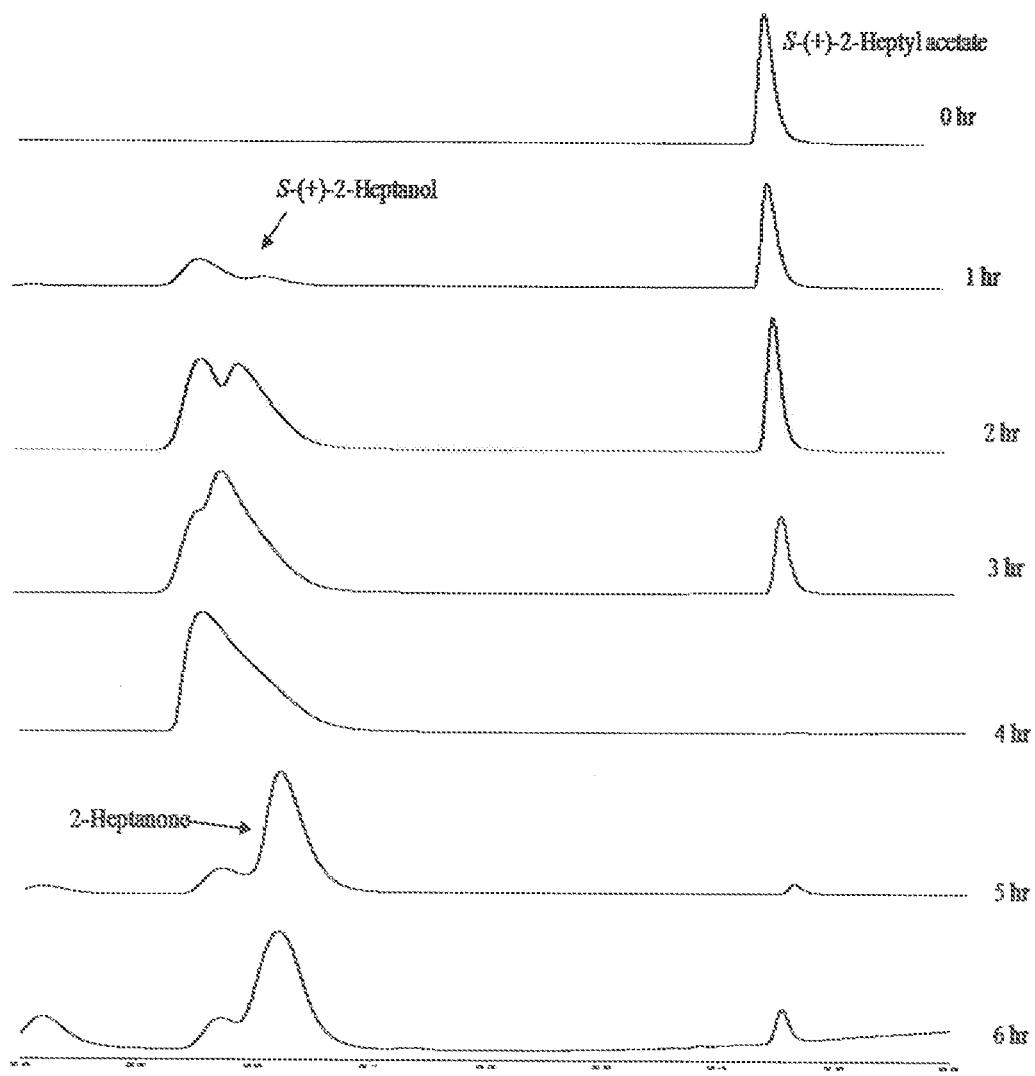
FIG. 6 is a GC chromatogram showing Resting cell experiment with S-(+)-2-Heptyl acetate.
Figure 7:
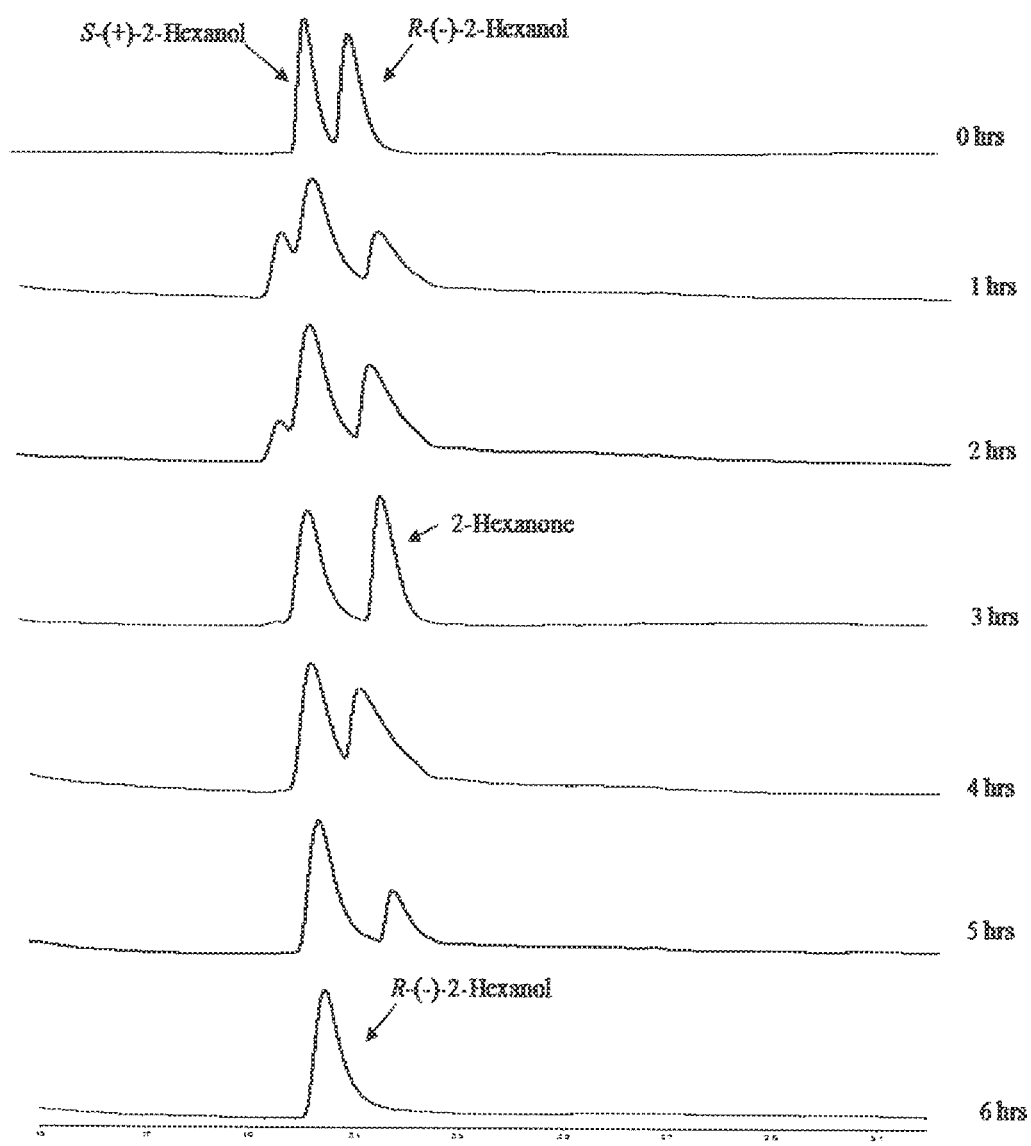
FIG. 7 is a GC chromatogram showing Resting cell experiment with (±)-2-Hexanol.
Figure 8:
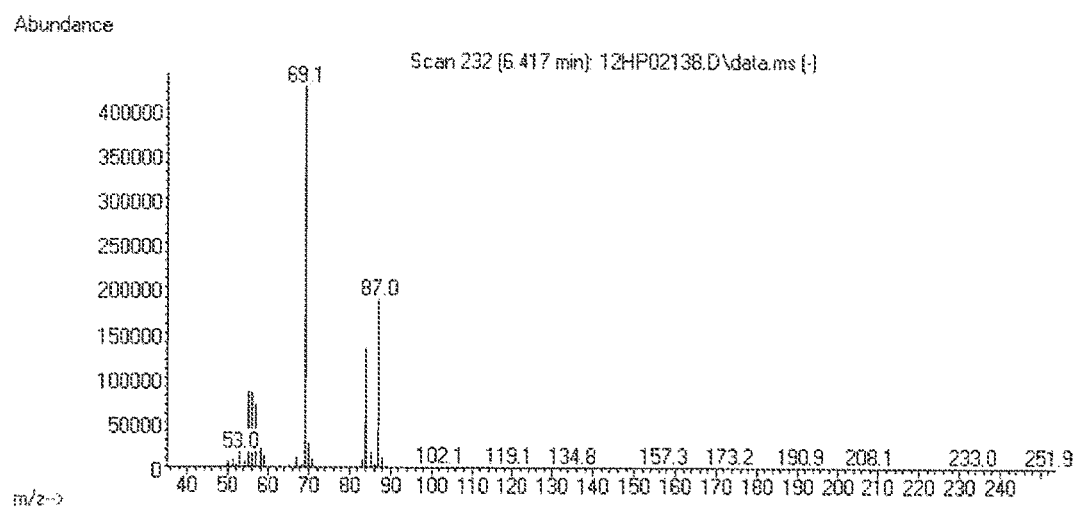
FIG. 8 is a Mass Fragmentation of (R)-(−)-2-Hexanol produced by *F. proliferatum* after conversion.
Figure 9:
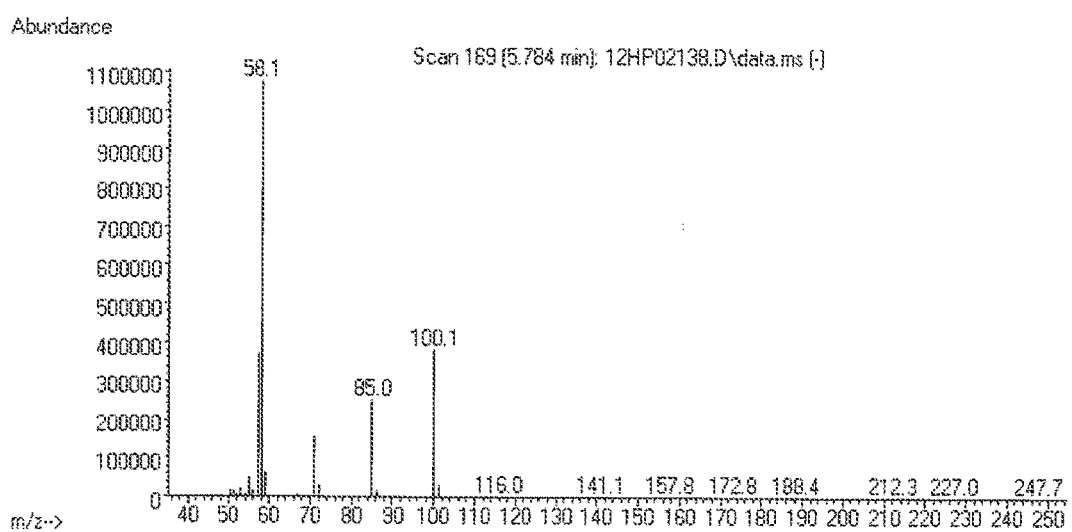
FIG. 9 is a Mass Fragmentation of 2-Hexanone produced by *F. proliferatum* after conversion.
Figure 10:
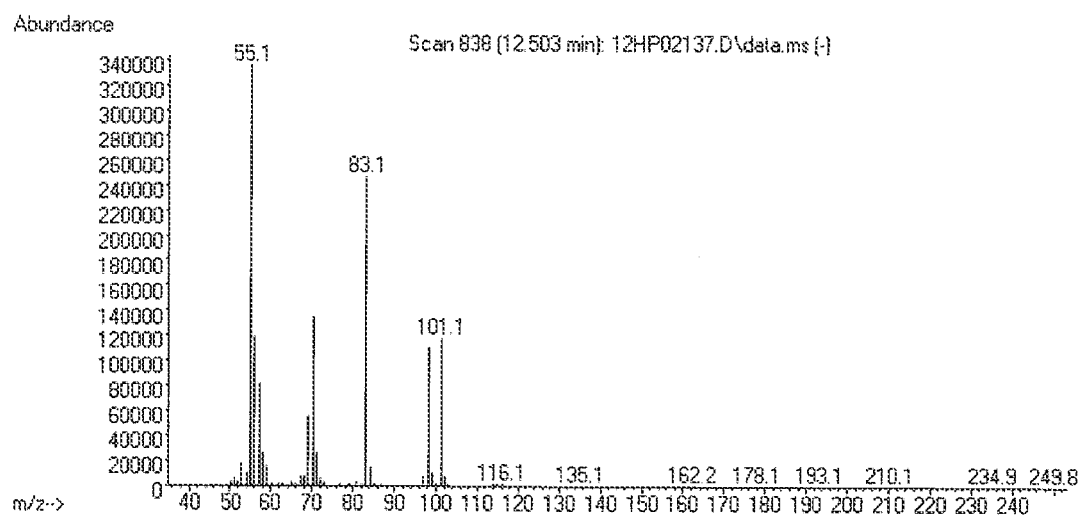
FIG. 10 is a Mass Fragmentation of (R)-(−)-2-Heptanol produced by *F. proliferatum* after conversion.
Figure 11:
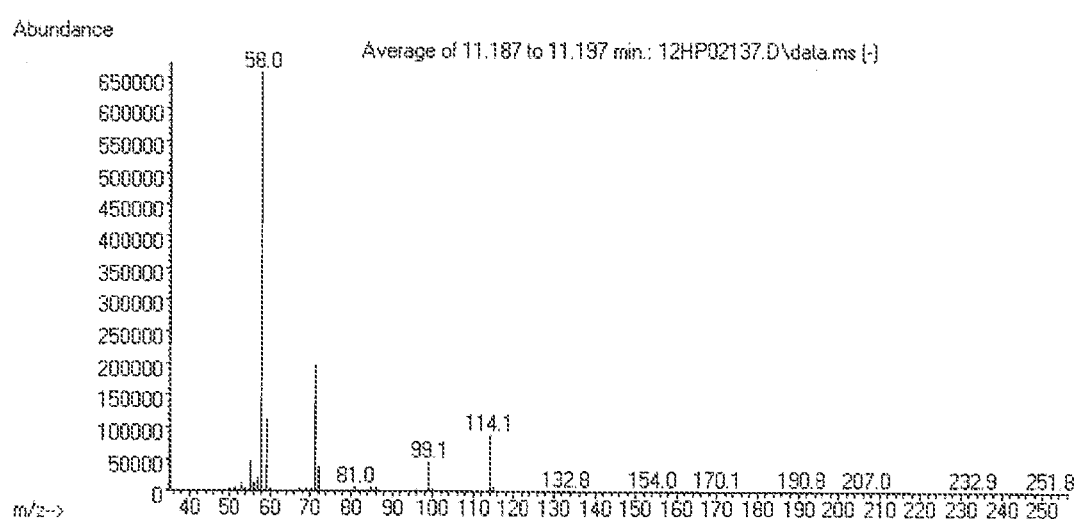
FIG. 11 is a Mass Fragmentation of 2-Heptanone produced by *F. proliferatum* after conversion.
Figure 12:
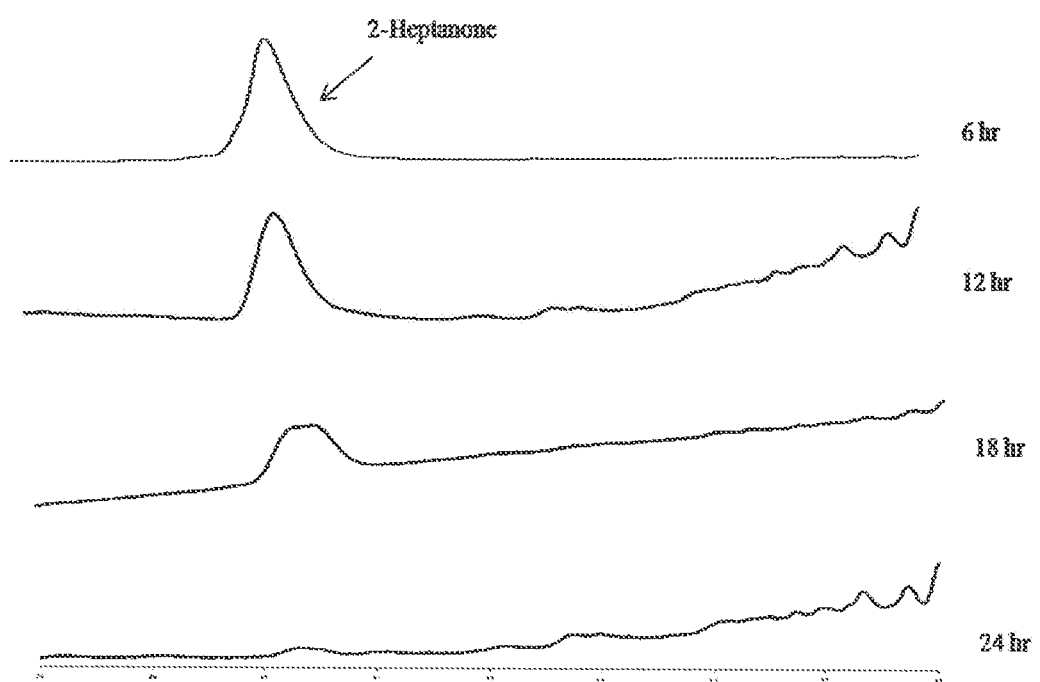
FIG. 12 is a GC chromatogram showing consumption of 2-Heptanone by *F. proliferatum* after 6, 12, 18 and 24 hrs.
Figure 13:
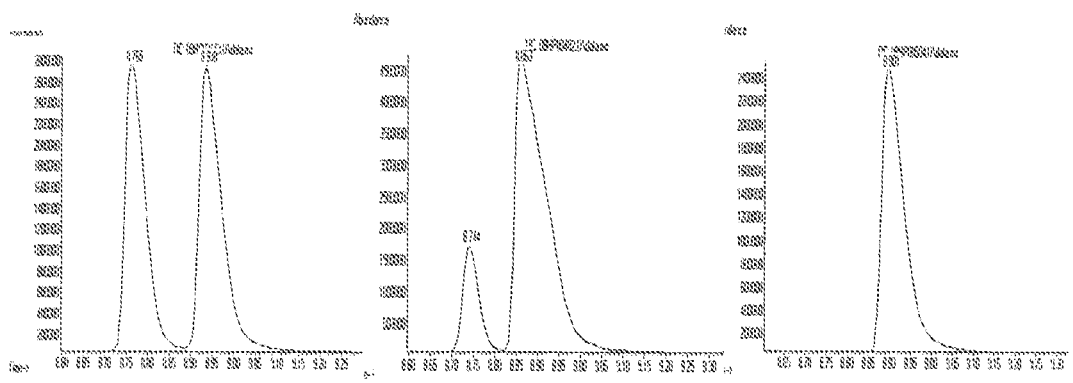
FIG. 13 is a GC-MS chromatogram showing consumption of single isomer (S) of Lavandulol. GC-MS chromatograms showing consumption of (S)-isomer of Lavandulol by *F. proliferatum* over a period of 1, 3 and 5 days.
Figure 14:
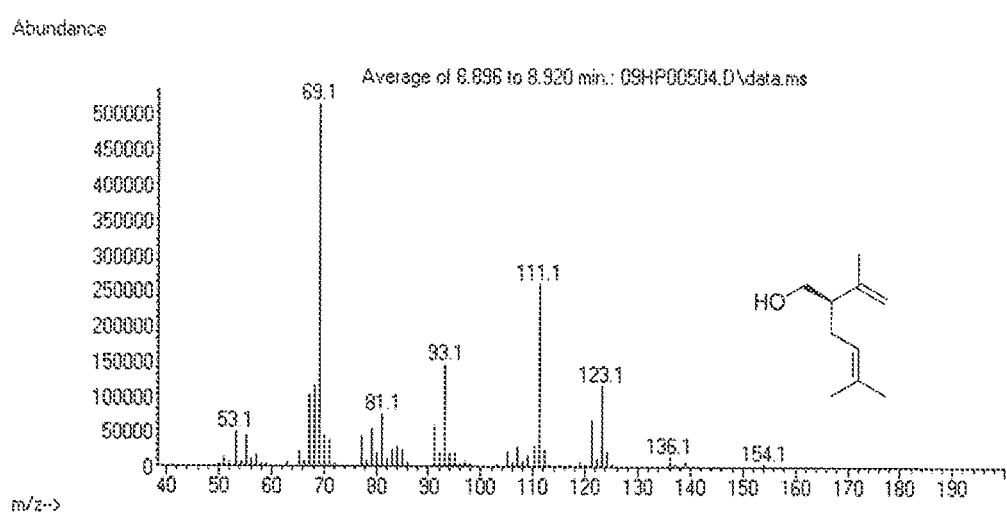
FIG. 14 is a Mass spectra of (R)-Lavandulol $[\alpha]_D$=10.12 (c=3 Chloroform), Mass spectra along with library search of (R)-Lavandulol
Figure 15:
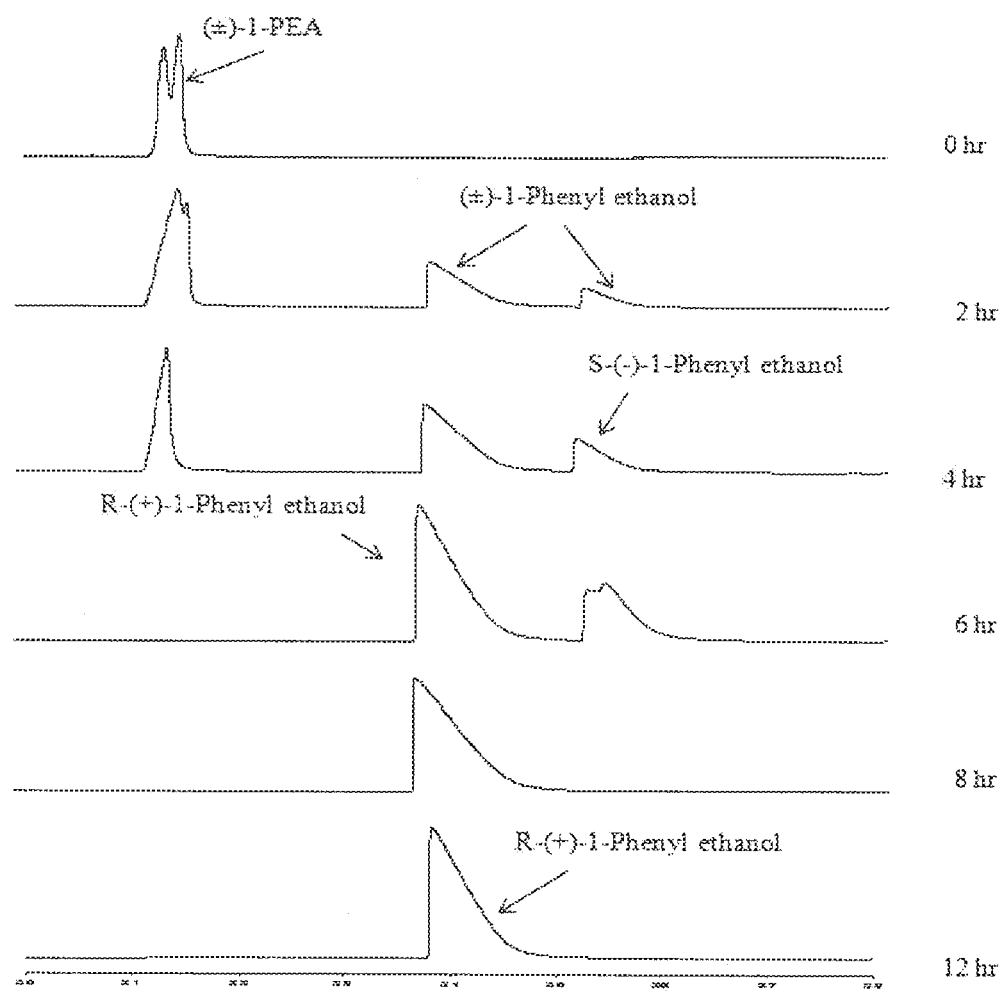
FIG. 15 is a GC chromatogram showing Resting cell experiment with (±)-1-Phenylethyl acetate.
Figure 16:
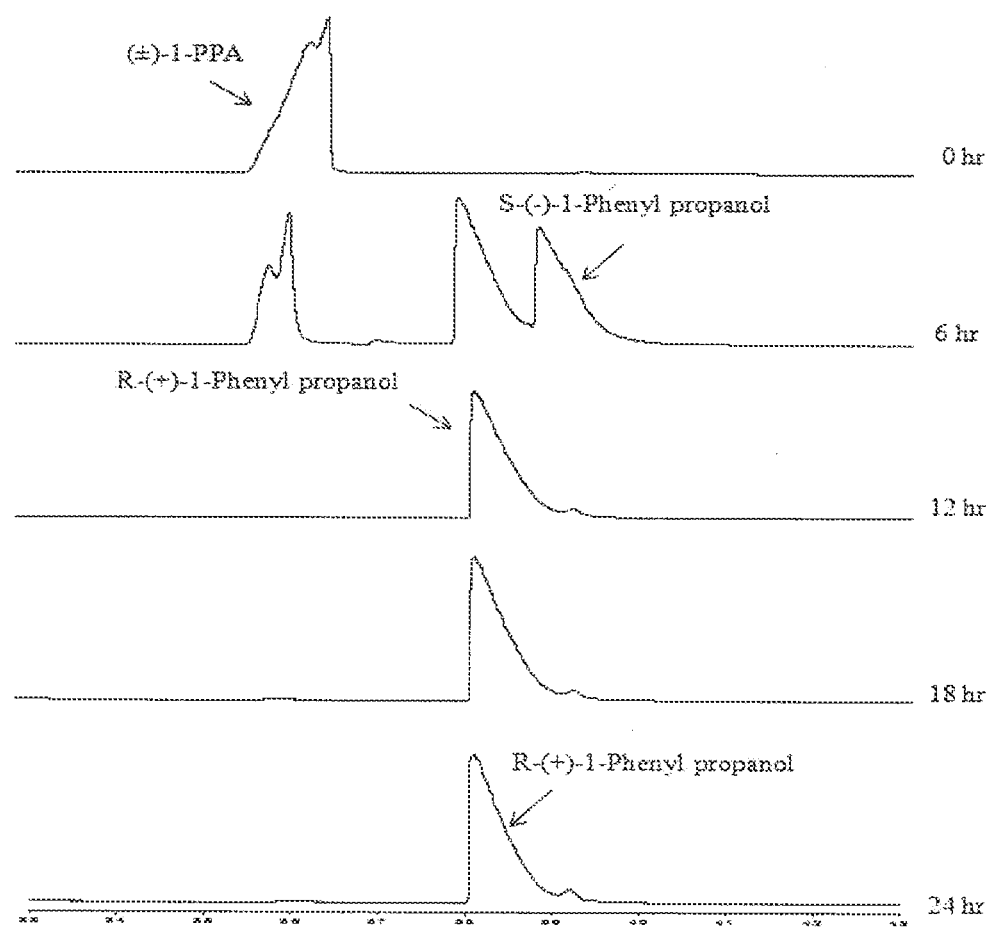
FIG. 16 is a GC chromatogram showing Resting cell experiment with (±)-1-Phenylpropyl acetate.

In view of above, the present invention provides an easier and cheaper process of producing enantiomerically pure R-Alcohols from racemic cyclic and acyclic acetates by whole cell method.

As used herein the term "chiral resolution" means not only separation but also going from racemic to single enantiomer.

According to the invention, whole cell microorganisms mean bacteria or fungal organisms or other microorganisms known to produce lipases εt Alcohol dehydrogenases.

In the present invention, fungal strains such as *F. proliferatum* is used for resolving racemic cyclic and acyclic acetates into (R)-Alcohols. Thus, this process can be used for the production of (R)-Alcohol from the racemic cyclic and acyclic acetate.

In an embodiment, the invention provides resolution of racemic cyclic and acyclic acetate to obtain enantiomerically pure (R)-Alcohol as single enantiomer through fungal catalyzed deacylation in single fermentation, wherein fungal strains selected is *F. proliferatum*.

The chiral resolution of racemic 2-Hexyl acetate to obtain enantiomerically pure (R)-2-Hexanol as a single enantiomer is represented as below Scheme 1:

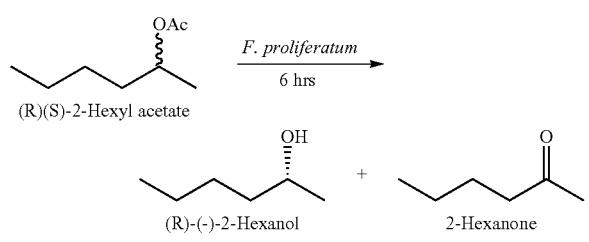

The chiral resolution of racemic 2-Heptyl acetate to obtain enantiomerically pure (R)-2-Heptanol as a single enantiomer is represented as below in Scheme 2:

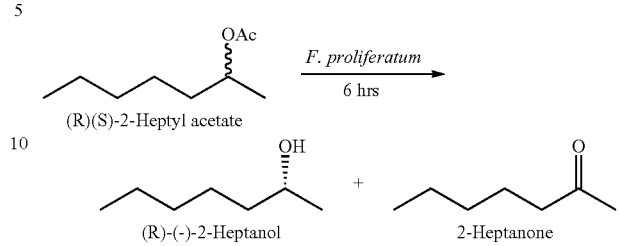

The chiral resolution of racemic lavandulyl acetate to obtain enantiomerically pure (R)-lavandulol as a single enantiomer is represented as depicted below in Scheme 3:

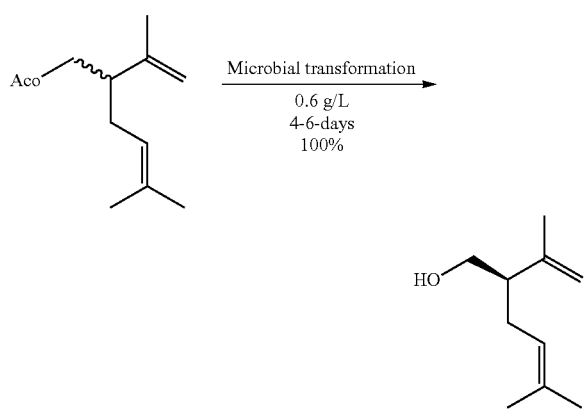

The chiral resolution of racemic 1-Phenylethyl acetate to obtain enantiomerically pure (R)-1-Phenylethanol as a single enantiomer is represented as depicted below in Scheme 4:

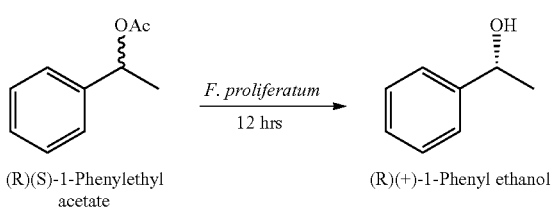

The chiral resolution of racemic 1-Phenylpropyl acetate to obtain enantiomerically pure (R)-1-Phenylpropanol as a single enantiomer is represented as depicted below in Scheme 5:

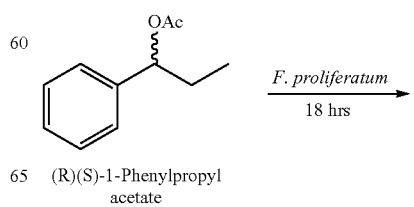

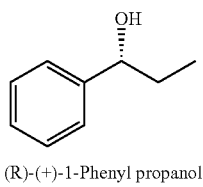

(R)-(+)-1-Phenyl propanol

In the present invention, the other isomer (S)-Alcohol has been converted to corresponding ketone and then it is further consumed by the fungus.

The preferential use of whole cells over enzymes as biocatalysts in the production of useful organic compounds mostly results from the costs of enzyme isolation, purification and stabilization in the latter method.

This method is simple and very useful for the production of (R)-Alcohols in large scale. Also it is cost effective as the process involves whole cell microorganisms. Advantage is no isolation and no purification needed.

Resting cell experiments showed that well grown fungi in modified Czapek Dox medium were able to resolve of racemic 2-Hexyl acetate (0.005 g), 2-Heptyl acetate (0.005 g), Lavandulyl acetate (0.005 g), 1-Phenylethyl acetate (0.005 g) and 1-Phenylpropyl acetate (0.005 g) in to (R)-2-Hexanol, (R)-2-Heptanol, (R)-Lavandulol, (R)-1-Phenylethanol and (R)-1-Phenylpropanol respectively in quantitative yield with respect to the ratio of racemic mixture This microorganism requires 6 hrs of incubation in resting cell experiments with 2-Hexyl acetate and 2-Heptyl acetate while racemic lavandulyl acetate requires 3 days for the complete transformation of by whole cell method and 24 hrs. by resting cell method. The remaining (S)-isomer of the alcohol has been converted to corresponding ketone by the organism.

GC-MS studies using chiral column showed the presence of only (R)-lavandulol and not any other metabolites.

EXAMPLES

Following examples are given by way of illustration therefore should not be construed to limit the scope of the invention.

Example 1

Enantiopure Preparation of R-(−)-Lavandulol from (±)-Lavandulyl Acetate Using *F. Proliferatum* by Whole Cell Method Into a 250 mL conical flask, 50 mL of modified Czapex Dox (C.Z) media pH-5.8 was taken and spores ($10^9$ per mL) of *F. proliferatum* (Deposition details: *Fusarium proliferatum* (NCIM cat No. 1105), OCT-F-25, Accession no: MCC0011) in water were added to it. Flasks were incubated for 48 hrs at temp 30° C. for their complete growth. In 3 flasks each containing fully grown fungus, substrate (±)-Lavandulyl acetate was added at concentration of 30 mg/50 mL) into it. Microorganism and substrate controls were also kept along with it( ). These flasks were incubated in incubator shaker at 30° C. and 200 rpm for 3 days and they were extracted at the interval of 1, 2, 3 days and analyzed by GC on Chiral column. At the end of 3 days, R-Lavandulol with more than 99% enantiopurity is formed. The confirmation study was done by co-injection of R-Lavandulol with extracted sample.

Example 2

Enantiopure Preparation of R-(−)-Lavandulol from (±)-Lavandulyl Acetate Using *F. Proliferatum* by Resting Cell Experiment Into a 250 mL conical flask, 50 mL of Potassium phosphate buffer with pH-7.2 in addition of 0.2% glucose was taken. 4 flasks each containing 2 gm of fungal mycelia for 50 mL of buffer was taken and the compound (±)-Lavandulyl acetate (5 mg) was added into it. Microorganism and substrate controls were also kept along with it.

These flasks were incubated in incubator shaker at 30° C. and 200 rpm. 4 Flasks along with controls were extracted at the interval of 6, 12, 18 and 24 hrs. and analyzed by GC on Chiral column. R-Lavandulol with more than 99% enantiopurity is formed at the end of 24 hrs. The confirmation study was done by co-injection of R-Lavandulol with extracted sample Example 3

Enantiopure Preparation of R-(−)-2-Hexanol from (±)-2-Hexyl Acetate Using *F. Proliferatum* by Resting Cell Experiment Into a 250 mL conical flask, 50 mL of Potassium phosphate buffer with pH-7.2 in addition of 0.2% glucose was taken. 4 flasks each containing 2 gm of fungal mycelia for 50 mL of buffer was taken and the compound (±)-2-Hexyl acetate (5 mg) was added into it. Microorganism and substrate controls were also kept along with it. These flasks were incubated in incubator shaker at 30° C. and 200 rpm. 4 Flasks along with controls were extracted at the interval of 1, 2, 3, 4, 5 and 6 hrs. and analyzed by GC on Chiral column. R-2-Hexanol with more than 99% enantiopurity is formed at the end of 6 hrs. The confirmation study was done by co-injection of R-2-Hexanol with extracted sample Example 4

Enantiopure Preparation of R-(−)-2-Heptanol from (±)-2-Heptyl Acetate Using *F. proliferatum* by Resting Cell Experiment Into a 250 mL conical flask, 50 mL of Potassium phosphate buffer with pH-7.2 in addition of 0.2% glucose was taken. 4 flasks each containing 2 gm of fungal mycelia for 50 mL of buffer was taken and the compound (±)-2-Heptyl acetate (5 mg) was added into it. Microorganism and substrate controls were also kept along with it.

These flasks were incubated in incubator shaker at 30° C. and 200 rpm. 4 Flasks along with controls were extracted at the interval of 1, 2, 3, 4, 5 and 6 hrs. and analyzed by GC on Chiral column. R-2-Heptanol with more than 99% enantiopurity is formed at the end of 6 hrs. The confirmation study was done by co-injection of R-2-Heptanol with extracted sample.

Example 5

Enantiopure Preparation of R-(+)-1-Phenyl Ethanol from (±)-1-Phenyl Ethyl Acetate Using *F. Proliferatum* by Resting Cell Experiment Into a 250 mL conical flask, 50 mL of Potassium phosphate buffer with pH-7.2 in addition of 0.2% glucose was taken. 4 flasks each containing 2 gm of fungal mycelia for 50 mL of buffer was taken and the compound (±)-1-Phenylethyl acetate (5 mg) was added into it. Microorganism and substrate controls were also kept along with it. These flasks were incubated in incubator shaker at 30° C. and 200 rpm. 4 Flasks along with controls were extracted at the interval of 2, 4, 6, 8, 10 and 12 hrs. and analyzed by GC on Chiral column. R-(+)-1-Phenyl ethanol with more than 99% enantiopurity is formed at the end of 12 hrs. The confirmation study was done by co-injection of R-(+)-1-Phenyl ethanol with extracted sample.

Example 6

Enantiopure Preparation of R-(+)-1-Phenyl Propanol from (±)-1-Phenyl Propyl Acetate Using *F. Proliferatum* by Resting Cell Experiment Into a 250 mL conical flask, 50 mL of Potassium phosphate buffer with pH-7.2 in addition of 0.2% glucose was taken. 4 flasks each containing 2 gm of fungal mycelia for 50 mL of buffer was taken and the compound (±)-1-Phenylpropyl acetate (5 mg) was added into it. Microorganism and substrate controls were also kept along with it. These flasks were incubated in incubator shaker at 30° C. and 200 rpm. 4 Flasks along with controls were extracted at the interval of 6.12, 18 and 24 hrs. and analyzed by GC on Chiral column. R-(+)-1-Phenyl propanol with more than 99% enantiopurity is formed at the end of 24 hrs. The confirmation study was done by co-injection of R-(+)-1-Phenyl propanol with extracted sample.

ADVANTAGES OF INVENTION a. This method is simple and very useful for the production of (R)-Alcohols in large scale.
b. Also it is cost effective as the process involves whole cell microorganisms.
c. No isolation and no purification needed.
d. The process can be used for Lavandulol which is an important constituent of essential oils and has been identified as a sex pheromone.
e. The process can be used for R-2-Hexanol/R-2-Heptanol which are important fragrance compounds and pharmaceutical intermediates used in various drug preparations.
f. The process can be used for R-1-Phenyl ethanol/R-1-Phenyl propanol which are very much important chiral drug intermediates and flavor compounds used in pharmaceutical and fragrance industry.

The invention claimed is:

1. A process for chiral resolution of a racemic acetate to obtain an enantiomerically pure (R)-Alcohol as a single enantiomer comprising the steps of:
   i) incubating *Fusarium proliferatum* for from 24 to 48 hours at a temperature between 28° C. to 30° C. in a medium;
   ii) adding the racemic acetate to the medium after step i) and incubating further for from 6 hours to 3 days at temperature between 28° C. to 30° C. to obtain the enantiomerically pure (R)-Alcohol.

2. The process according to claim 1, wherein the *Fusarium proliferatum* comprises spores and mycelia.

3. The process according to claim 1, wherein the racemic acetate is selected from the group consisting of 2-Heptyl acetate, lavandulyl acetate and 2-Hexyl acetate.

4. The process according to claim 1, wherein the racemic acetate is a cyclic racemic acetate or an acyclic racemic acetate.

5. The process according to claim 1, wherein a yield of the enantiomerically pure (R)-Alcohol as a single enantiomer is 95-99.9%.

6. The process according to claim 1, wherein the enantiomerically pure (R)-Alcohol is selected from the group consisting of R-lavandulol, R-2-Hexnol, R-2-Heptanol, R-1-Phenyl ethanol and R-1-Phenyl propanol.

* * * * *